(12) United States Patent
Voronov et al.

(10) Patent No.: US 8,717,555 B2
(45) Date of Patent: May 6, 2014

(54) DEVICE AND METHOD FOR INSPECTING POLYCRYSTALLINE SILICON LAYER

(75) Inventors: Alexander Voronov, Yongin (KR); Suk-Ho Lee, Yongin (KR); Jae-Seung Yoo, Yongin (KR); Kyung-Hoe Heo, Yongin (KR); Gyoo-Wan Han, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 374 days.

(21) Appl. No.: 13/214,272

(22) Filed: Aug. 22, 2011

(65) Prior Publication Data
US 2012/0057148 A1 Mar. 8, 2012

(30) Foreign Application Priority Data
Sep. 7, 2010 (KR) .................. 10-2010-0087596

(51) Int. Cl.
*G01N 21/00* (2006.01)
(52) U.S. Cl.
USPC .................. 356/237.1; 356/239.1; 356/239.3; 356/239.7; 356/237.4
(58) Field of Classification Search
USPC .................. 356/237.1–241.6, 242.1–243.8, 356/426–431, 600–640
See application file for complete search history.

(56) References Cited

U.S. PATENT DOCUMENTS

| 5,293,216 A * | 3/1994 | Moslehi ..................... 356/600 |
| 6,700,663 B1 | 3/2004 | Lin |
| 6,798,498 B2 | 9/2004 | Wada et al. |
| 6,806,099 B2 * | 10/2004 | Takeda et al. ................. 438/7 |
| 6,975,386 B2 | 12/2005 | Tsumura et al. |
| 7,184,132 B2 * | 2/2007 | Tsao .......................... 356/30 |
| 7,505,155 B2 * | 3/2009 | Jang et al. .................... 356/634 |
| 2003/0017658 A1 * | 1/2003 | Nishitani et al. ............ 438/149 |
| 2004/0115337 A1 | 6/2004 | Tsao et al. |
| 2005/0002016 A1 | 1/2005 | Tsao |
| 2005/0174569 A1 | 8/2005 | Jang et al. |

FOREIGN PATENT DOCUMENTS

| JP | 2002-289522 A | 10/2002 |
| JP | 2005-129679 A | 5/2005 |
| KR | 10-1999-0072437 A | 9/1999 |

* cited by examiner

*Primary Examiner* — Gregory J Toatley
*Assistant Examiner* — Jarreas C Underwood
(74) *Attorney, Agent, or Firm* — Lee & Morse, P.C.

(57) ABSTRACT

A device for inspecting a polycrystalline silicon layer that is crystallized by receiving irradiated laser beams on a front side of the polycrystalline silicon layer includes: a light source configured to emit inspection beams to a rear side of the polycrystalline silicon layer; a light inspector configured to inspect the inspection beams reflected at the rear side of the polycrystalline silicon layer; and a controller that controls the light source and the light inspector.

22 Claims, 6 Drawing Sheets

DEVICE AND METHOD FOR INSPECTING POLYCRYSTALLINE SILICON LAYER

BACKGROUND

1. Field

The described technology relates generally to a polycrystalline silicon layer inspecting device and inspecting method. More particularly, the described technology relates generally to a device for inspecting crystallinity or crystal particles of a polycrystalline silicon layer, and an inspecting method thereof.

2. Description of the Related Art

Most flat panel display devices, such as an organic light emitting diode (OLED) display, a liquid crystal display (LCD), and the like, include a thin film transistor. Particularly, a low temperature polycrystalline silicon thin film transistor (LTPS TFT) having good carrier mobility can be applicable to a high speed operational circuit and can be used for a CMOS circuit, so the LPTS TFT has been commonly used.

The LTPS TFT includes a polycrystalline silicon film that is formed by crystallizing an amorphous silicon film. Methods for crystallizing the amorphous silicon film include a solid phase crystallization method, an excimer laser beams crystallization method, and a crystallization method using a metal catalyst.

Among various crystallization methods, a crystallization method using laser beams has been widely used because it enables a low temperature process so that a thermal effect on a substrate is relatively low and enables making a polycrystalline silicon layer having relatively excellent carrier mobility as high as over 100 $cm^2/Vs$.

The above information disclosed in this Background section is only for enhancement of understanding of the background of the described technology and therefore it may contain information that does not form the prior art that is already known in this country to a person of ordinary skill in the art.

SUMMARY

According to an embodiment, there is provided a device for inspecting a polycrystalline silicon layer that is crystallized by receiving irradiated laser beams on a front side of the polycrystalline silicon layer. The device includes a light source configured to emit inspection beams to a rear side of the polycrystalline silicon layer, a light inspector configured to inspect the inspection beams reflected on the polycrystalline silicon layer, and a controller for controlling the light source and the light inspector.

The front side of the polycrystalline silicon layer may include a plurality of crystallized protrusions. The rear side of the polycrystalline silicon layer may contact a buffer layer or a substrate and is parallel with the buffer layer or substrate.

The polycrystalline silicon layer may be crystallized starting from the front side. An area near the rear side of the polycrystalline silicon layer is in an amorphous or microcrystalline state.

The laser beams crystallizing the polycrystalline silicon layer may be excimer laser beams.

The buffer layer or the substrate may be made of a material including silicon.

The buffer layer or the substrate, together with the polycrystalline silicon layer, may have a transmittance that is greater than 5%.

The polycrystalline silicon layer may have a thickness within the range of 10 nm to 300 nm.

The inspection beams may include at least one of ultraviolet (UV) rays, infrared rays, and laser beams.

A wavelength with a reflective index that is less than 50% from among the inspection beams in the polycrystalline silicon layer may be used for measurement.

A wavelength for measuring the polycrystalline silicon layer from among the inspection beams may be greater than 385 nm and equal to or less than 410 nm.

The polycrystalline silicon layer may be measured by at least one of reflectivity measurement, Raman spectroscopy, and spectroscopic ellipsometry.

According to an embodiment, there is provided a method for inspecting a polycrystalline silicon layer that is crystallized by receiving irradiated laser beams on a front side of the polycrystalline silicon layer. The method includes emitting inspection beams to a rear side of the polycrystalline silicon layer, and inspecting and analyzing the inspection beams reflected on the polycrystalline silicon layer.

The front side of the polycrystalline silicon layer may include a plurality of crystallized protrusions, and the rear side of the polycrystalline silicon layer may contact a buffer layer or a substrate and may be parallel with the buffer layer or substrate.

The polycrystalline silicon layer may be crystallized starting from the front side. An area near the rear side of the polycrystalline silicon layer may be in an amorphous or microcrystalline state.

The laser beams crystallizing the polycrystalline silicon layer may be excimer laser beams.

The buffer layer or the substrate may be made of a material including silicon.

The buffer layer or the substrate, together with the polycrystalline silicon layer, may have transmittance that is greater than 5%.

The polycrystalline silicon layer may have a thickness within the range of 10 nm to 300 nm.

The inspection beams may include at least one of ultraviolet (UV) rays, infrared rays, and laser beams.

A wavelength with a reflective index that is less than 50% from among the inspection beams in the polycrystalline silicon layer may be used for measurement.

A wavelength used to measure the polycrystalline silicon layer from among the inspection beams may be greater than 385 nm and equal to or less than 410 nm.

The polycrystalline silicon layer may be measured by using at least one of reflectivity measurement, Raman spectroscopy, and spectroscopic ellipsometry.

According to an embodiment, there is provided a combination including a polycrystalline silicon layer that is crystallized by receiving irradiated laser beams on a front side of the polycrystalline silicon layer, and a device that inspects the polycrystalline silicon layer, wherein the polycrystalline silicon layer and the device that inspects the polycrystalline silicon layer are oriented with respect to each other such that a light source of the device emits inspection beams to a rear side of the polycrystalline silicon layer and a light inspector of the device inspects the inspection beams after the inspection beams are reflected on the polycrystalline silicon layer, and wherein the device includes a controller for controlling the light source and the light inspector.

BRIEF DESCRIPTION OF THE DRAWINGS

The above and other features and advantages will become more apparent to those of ordinary skill in the art by describing in detail exemplary embodiments with reference to the attached drawings, in which.

DETAILED DESCRIPTION

Figure 1:
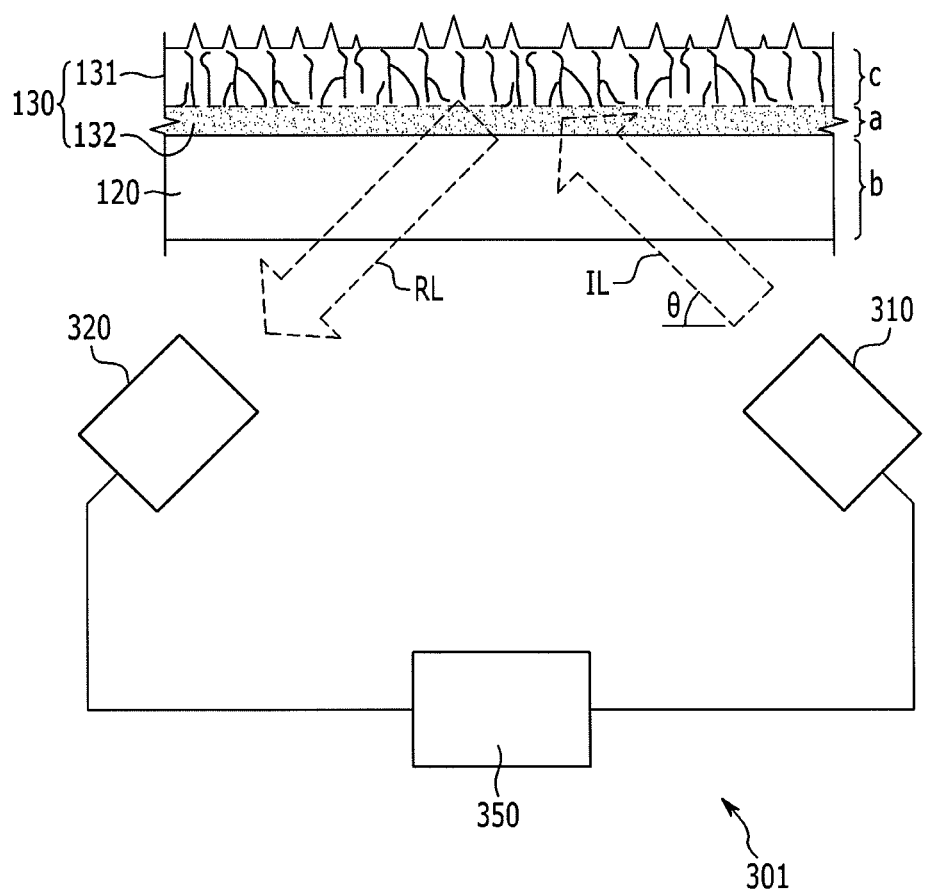
FIG. 1 illustrates a schematic diagram of a polycrystalline silicon layer inspecting device according to an exemplary embodiment.

Korean Patent Application No. 10-2010-0087596, filed on Sep. 7, 2010, in the Korean Intellectual Property Office, and entitled: "Device and Method for Inspecting Polycrystaline Silicon Layer," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

A polycrystalline silicon layer inspecting device 301 according to an exemplary embodiment will now be described with reference to FIG. 1.

As shown in FIG. 1, the polycrystalline silicon layer inspecting device 301 includes a light source 310, a light inspector 320, and a controller 350.

A polycrystalline silicon layer 130 inspected by using the polycrystalline silicon layer inspecting device 301 according to an exemplary embodiment is crystallized by receiving the irradiated laser beams on the front side of the polycrystalline silicon layer 130. In this instance, excimer laser beams may be used. Also, the polycrystalline silicon layer 130 is crystallized starting from its front side to which the laser beams are irradiated, and a plurality of crystallized protrusions are formed on the front side during crystallization. The rear side of the polycrystalline silicon layer 130 touches a buffer layer 120 or a substrate (not shown), and is formed to be parallel with the same. The buffer layer 120 or the substrate may be made of a material including silicon (Si). For convenience of description, FIG. 1 shows the buffer layer 120. A substrate other than the buffer layer 120 may be present, or both the buffer layer 120 and the substrate may be present.

The buffer layer 120 or the substrate together with the polycrystalline silicon layer 130 has transmittance of over 5%. The polycrystalline silicon layer 130 may have a thickness of 10 nm to 300 nm. When the transmittance and the thickness are out of these ranges, the polycrystalline silicon layer inspecting device 301 may not be able to accurately inspect the polycrystalline silicon layer 130.

A predetermined area near the rear side of the polycrystalline silicon layer 130 can be amorphous or microcrystalline. That is, the polycrystalline silicon layer 130 may include a completely crystallized polycrystalline layer 131 and an amorphous layer 132 that is not completely crystallized. Also, a microcrystalline layer (not shown) may be formed other than the amorphous layer 132, or the amorphous layer 132 and the microcrystalline layer may be mixed.

In FIG. 1, "a: represents the thickness of the amorphous layer, "b" is the thickness of the buffer layer, and "c" indicates the thickness of the polycrystalline layer.

The polycrystalline silicon layer inspecting device 301 can efficiently and precisely detect an area where the polycrystalline silicon layer 130 is not completely crystallized but remains as amorphous or microcrystalline.

The light source 310 emits inspection beams (IL) to the rear side of the polycrystalline silicon layer 130. The light inspector 320 inspects the inspection beams (RL) reflected on the polycrystalline silicon layer 130. The controller 350 controls the light source 310 and the light inspector 320. That is, the controller 350 controls the light of the light source 310 and analyzes the inspection beams inspected by the light inspector 320.

A plurality of crystallized protrusions are formed on the front side of the polycrystalline silicon layer 130 during crystallization. The front side of the polycrystalline silicon layer 130 has relatively greater roughness. Therefore, if the light source 310 were to emit inspection beams (IL) to the front side of the polycrystalline silicon layer 130, the inspection beams (IL) might be scattered by the crystallized protrusions and it might be difficult for the polycrystalline silicon layer inspecting device 301 to perform a precise measurement process in a stable manner.

However, the polycrystalline silicon layer inspecting device 301 according to the present embodiment irradiates the inspection beams (IL) to the rear side of the polycrystalline silicon layer 130, that is, to a flat side where no crystallized protrusions are formed, and inspects the polycrystalline silicon layer 130. Therefore, the polycrystalline silicon layer inspecting device 301 can precisely and stably inspect the polycrystalline silicon layer 130.

The inspection beams (IL) may include at least one of ultraviolet (UV) rays, infrared rays, and laser beams. The types of the inspection beams (IL) follow the measurement method used.

The polycrystalline silicon layer inspecting device 301 uses at least one of reflectivity measurement, Raman spectroscopy, and spectroscopic ellipsometry as methods for measuring the polycrystalline silicon layer 130. That is, various methods may be used when the inspection beams (IL) are irradiated to the rear side of the polycrystalline silicon layer 130.

The inspection beams (IL) may be irradiated to the polycrystalline silicon layer 130 with various incidence angles (θ) depending on the measurement method.

The polycrystalline silicon layer 130 may be inspected in a precise and stable manner according to the above-described configuration.

Figure 2:
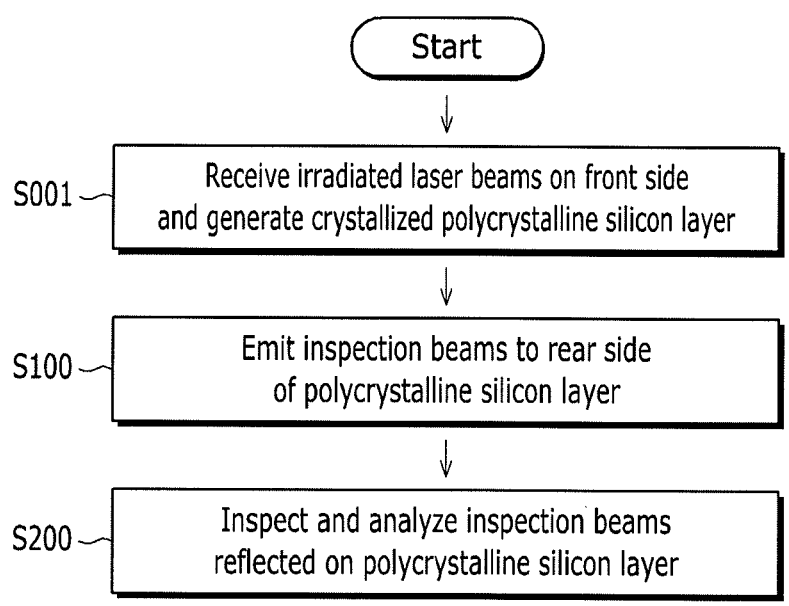
FIG. 2 illustrates a flowchart of a polycrystalline silicon layer inspecting method according to an exemplary embodiment.

A polycrystalline silicon layer inspecting method according to an exemplary embodiment will now be described with reference to FIG. 1 and FIG. 2.

A polycrystalline silicon layer 130 is crystallized by irradiating the laser beams to the front side is provided (S001). A plurality of crystallized protrusions are formed on the front side of the polycrystalline silicon layer 130. The inspection beams (IL) are emitted to the rear side of the polycrystalline silicon layer 130 (S100). The wavelength of the inspection beams (IL) with the reflective index that is less than 50% may be used for the polycrystalline silicon layer 130. In detail, the wavelength used for measuring the polycrystalline silicon layer from among the inspection beams (IL) may be greater than 385 nm and less than 410 nm. The inspection beams (RL) reflected on the polycrystalline silicon layer 130 are inspected and analyzed (S200).

Through the above-described polycrystalline silicon layer inspecting method, the polycrystalline silicon layer 130 may be inspected precisely and stably.

Figure 3:
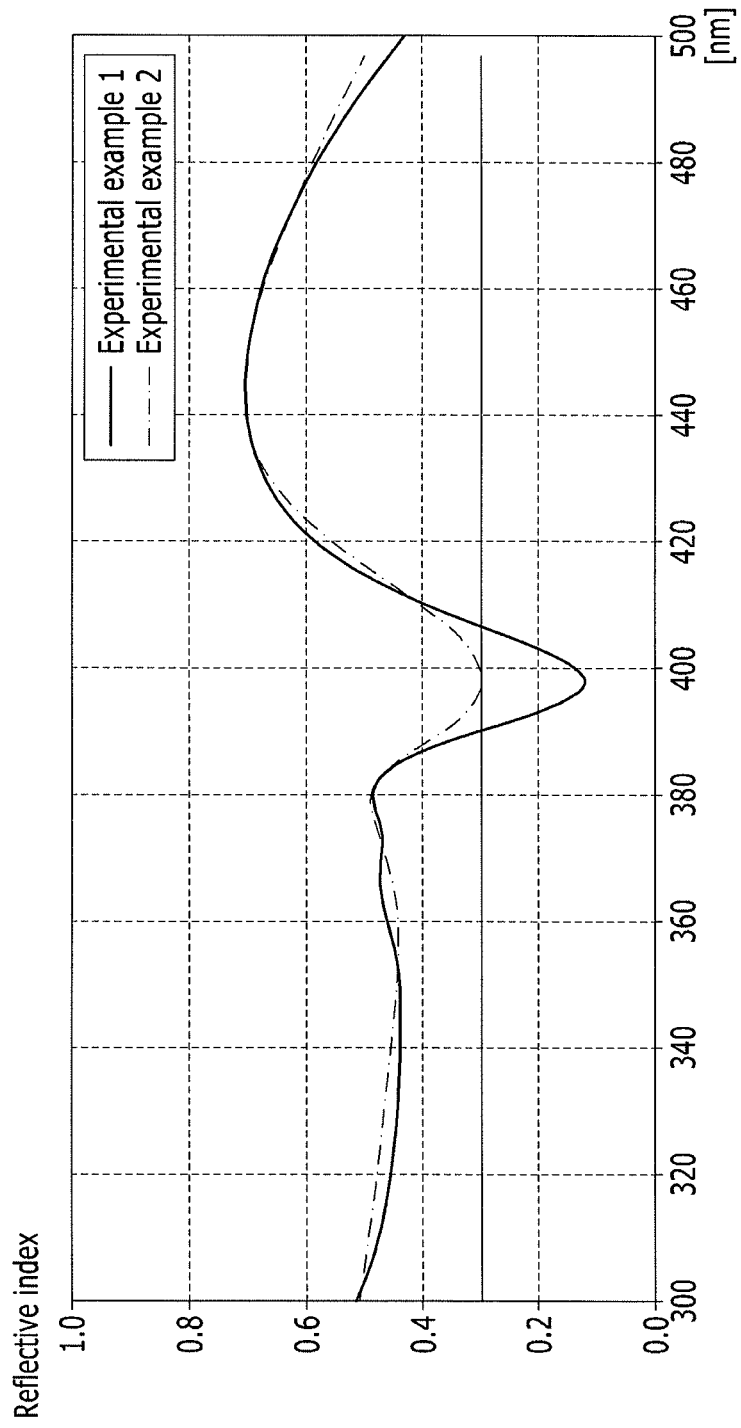
FIG. 3 and FIG. 4 illustrate graphs acquired by a polycrystalline silicon layer inspecting method according to an exemplary embodiment.
Figure 4:
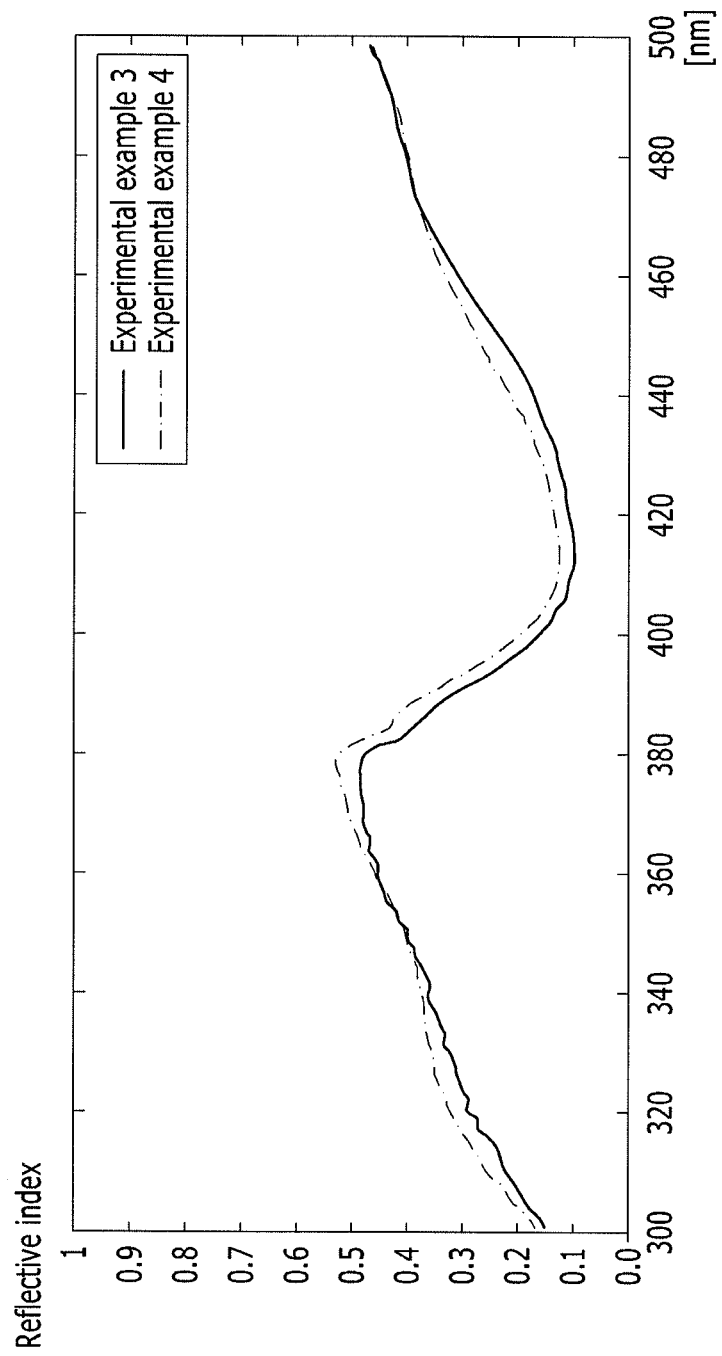

Experiments acquired by measuring a reflective index of the polycrystalline silicon layer by using a polycrystalline silicon layer inspecting device and inspecting method according to an exemplary embodiment will now be described with reference to FIG. 3 and FIG. 4. FIG. 3 and FIG. 4 show graphs acquired by measuring the reflective index of the polycrystalline silicon layer according to the polycrystalline silicon layer inspecting method according to an exemplary embodiment.

In the experiments, the reflective index of the polycrystalline silicon layer formed on the buffer layer of $SiO_2$ is measured by the polycrystalline silicon layer inspecting method according to an exemplary embodiment. In this instance, the incidence angle of the inspection beams is 45 degrees.

In the first experiment, in the case of Experimental Example 1, the polycrystalline silicon layer includes a polycrystalline layer with a thickness of 40 nm and an amorphous layer with a thickness of 1 nm. In the case of Experimental Example 2, the polycrystalline silicon layer includes a polycrystalline layer with a thickness of 40 nm and an amorphous layer with a thickness of 10 nm. Experimental Example 1 and Experimental Example 2 have the same conditions, except that the thickness of the amorphous layer of the polycrystalline silicon layer differs.

As shown in FIG. 3, the graph of Experimental Example 1 and the graph of Experimental Example 2 show distinctively distinguished reflective indexes at the wavelength between 385 nm and 410 nm. That is, the reflective index of the polycrystalline silicon layer of Experimental Example 1, with a relatively thinner amorphous layer, is relatively less than that of Experimental Example 2.

Accordingly, crystallinity of the polycrystalline silicon layer can be precisely inspected according to the polycrystalline silicon layer inspecting method according to an exemplary embodiment. In detail, it is possible to precisely and stably detect the thickness of the layer that remains not completely crystallized but is amorphous or microcrystalline in the polycrystalline silicon layer.

When the polycrystalline silicon layer is formed by irradiating the excimer laser beams to the amorphous silicon layer and crystallizing the amorphous silicon layer, crystallinity is increased as energy density of the laser beams is increased or the time for irradiating the laser beams is increased. However, when the energy density of the laser beams or the laser beams irradiation time is excessively increased, the roughness of the front side caused by the crystallized protrusions is abruptly increased and loss is increased during the process. On the other hand, when the energy density of the laser beams or the laser beams irradiation time is excessively decreased, crystallinity is reduced and the area in the amorphous state is increased. When the crystallinity of the polycrystalline silicon layer is substantially reduced, the required characteristics may not be provided.

With the polycrystalline silicon layer inspecting device and inspecting method according to an exemplary embodiment, crystallinity and crystal particles of the polycrystalline silicon layer can be precisely and stably measured without being influenced by the crystallized protrusions.

However, in practice, the thickness of the layer remaining as amorphous or microcrystalline rather than being completely crystallized may not be uniformly formed in the polycrystalline silicon layer. The next experiment is performed by using polycrystalline silicon layers with different energy densities of the laser beams used for crystallization.

In the second experiment, in the case of Experimental Example 3, the polycrystalline silicon layer is crystallized by irradiating the laser beams to the amorphous silicon layer with energy density of 400 $mJ/cm^2$. In the case of Experimental Example 4, the polycrystalline silicon layer is crystallized by irradiating the laser beams to the amorphous silicon layer with energy density of 402 $mJ/cm^2$. Except for the difference in the energy density of the laser beams, Experimental Example 3 and Experimental Example 4 have the same conditions. A buffer layer made of $SiO_2$ with a thickness of 300 nm is included, and the polycrystalline silicon layer has a thickness of 45 nm. The incidence angle of the inspection beams is 45 degrees.

As shown in the graph of Experimental Example 3 and the graph of Experimental Example 4 of FIG. 4, the difference of energy density is 2 $mJ/cm^2$ and the reflective index is clearly distinguished over the whole wavelength, particularly within the range from 380 nm to 420 nm. The reflective index of polycrystalline silicon layer crystallized through the laser beams with relatively low energy density is measured to be high.

According to the polycrystalline silicon layer inspecting method, the difference in the reflective index of the polycrystalline silicon layers due to a difference in the energy density of the laser beams used to crystallize the polycrystalline silicon layers may be measured precisely and stably.

Figure 5:
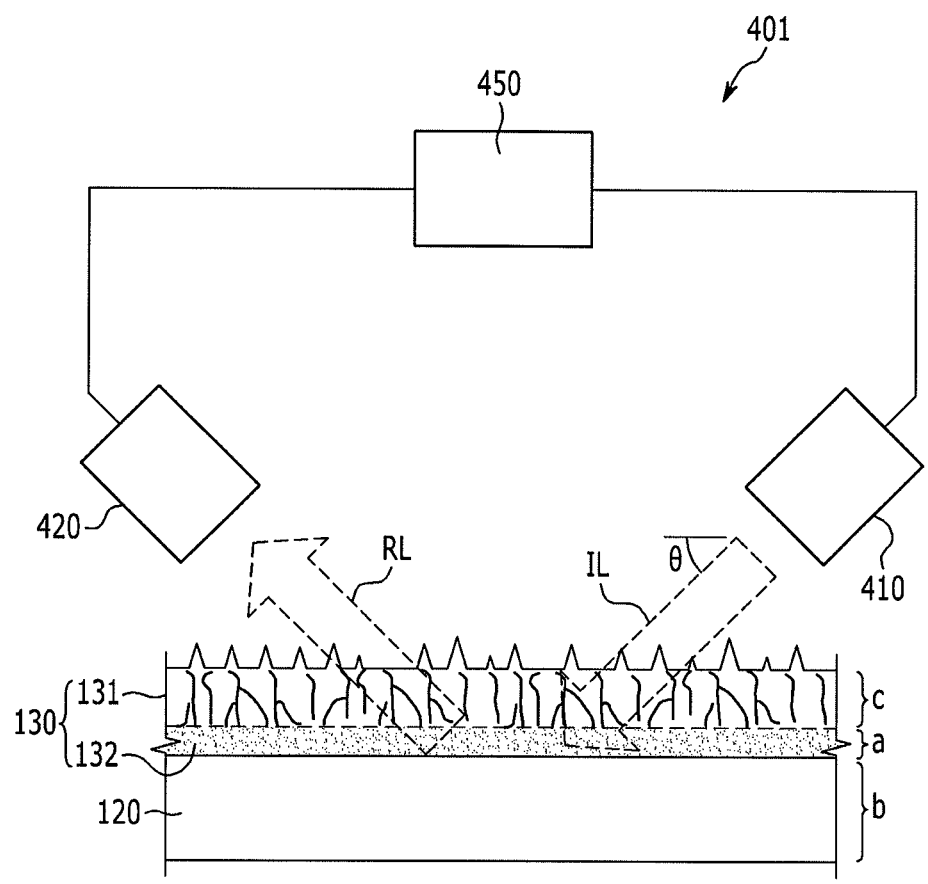
FIG. 5 illustrates a schematic diagram of a polycrystalline silicon layer inspecting device following a comparative example.

FIG. 5 shows a schematic diagram of a polycrystalline silicon layer inspecting device 401 according to a comparative example. The polycrystalline silicon layer inspecting device 401 according to the comparative example irradiates inspection beams (IL) to the front side of the polycrystalline silicon layer 130, that is, the side on which a plurality of crystallized protrusions are formed.

Figure 6:
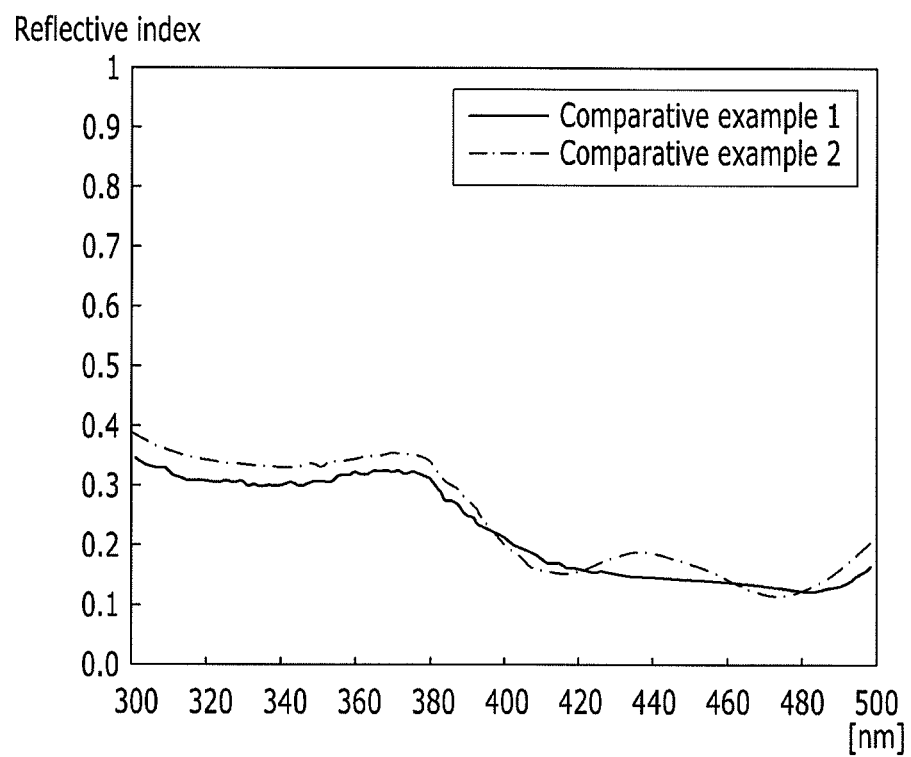
FIG. 6 illustrates a graph acquired by a polycrystalline silicon layer inspecting device of FIG. 5.

FIG. 6 shows a graph acquired by measuring a polycrystalline silicon layer 130 by using a polycrystalline silicon layer inspecting device 401 of FIG. 5.

Comparative Example 1 shows measurement results of the reflective index of the polycrystalline silicon layer with the same conditions as Experimental Example 3, except for the irradiation direction of the inspection beams. Further, Comparative Example 2 shows measurement results of the reflective index of the polycrystalline silicon layer with the same conditions as Experimental Example 4, except for the irradiation direction of the inspection beams.

As shown in the graph of Comparative Example 1 and the graph of Comparative Example 2 provided in FIG. 6, the reflective index of the polycrystalline silicon layer crystallized through the laser beams with relatively low energy density and the reflective index of the polycrystalline silicon layer crystallized through the laser beams with relatively high energy density cannot be clearly identified, particularly within the range from 380 nm to 420 nm. The reflective index of the polycrystalline silicon layer crystallized through the laser beams with relatively low energy density is shown to be higher in some wavelengths whereas the reflective index of the polycrystalline silicon layer crystallized through the laser beams with relatively high energy density is shown to be higher in some other wavelengths.

By way of summation and review, to check whether the polycrystalline silicon layer is appropriately crystallized, inspection beams may be irradiated to the polycrystalline silicon layer to inspect crystallinity or crystal particles of the polycrystalline silicon layer.

A plurality of crystallized protrusions may be formed in a polycrystalline silicon layer that is crystallized by irradiation of laser beams. When the intensity of the laser beams is reinforced so as to increase crystallinity of the polycrystalline silicon layer, the front side roughness of the polycrystalline silicon layer is increased by the crystallized protrusions. The embodiment disclosed herein circumvents scattering of the inspection beams by the crystallized protrusions, thereby avoiding errors when the crystallinity or crystal particles of the polycrystalline silicon layer are inspected.

The polycrystalline silicon layer inspecting device and the inspecting method can precisely and stably inspect the polycrystalline silicon layer through the above-described various experimental examples and comparative examples.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A device for inspecting a polycrystalline silicon layer that is crystallized by receiving irradiated laser beams on a front side of the polycrystalline silicon layer, the device comprising:
   a light source configured to emit inspection beams to a rear side of the polycrystalline silicon layer, wherein the front side of the polycrystalline silicon layer includes a plurality of crystallized protrusions;
   a light inspector configured to inspect the inspection beams reflected on the polycrystalline silicon layer; and
   a controller for controlling the light source and the light inspector.

2. The device as claimed in claim 1, wherein
the rear side of the polycrystalline silicon layer contacts a buffer layer or a substrate and is parallel with the buffer layer or substrate.

3. The device as claimed in claim 2, wherein
the polycrystalline silicon layer is crystallized starting from the front side, and
an area near the rear side of the polycrystalline silicon layer is in an amorphous or microcrystalline state.

4. The device as claimed in claim 2, wherein
the laser beams crystallizing the polycrystalline silicon layer are excimer laser beams.

5. The device as claimed in claim 2, wherein
the buffer layer or the substrate is made of a material including silicon.

6. The device as claimed in claim 2, wherein
the buffer layer or the substrate, together with the polycrystalline silicon layer, has transmittance that is greater than 5%.

7. The device as claimed in claim 1, wherein
the polycrystalline silicon layer has a thickness within the range of 10 nm to 300 nm.

8. The device as claimed in claim 1, wherein
the inspection beams include at least one of ultraviolet (UV) rays, infrared rays, and laser beams.

9. The device as claimed in claim 8, wherein
a wavelength with a reflective index that is less than 50% from among the inspection beams in the polycrystalline silicon layer is used for measurement.

10. The device as claimed in claim 8, wherein
a wavelength for measuring the polycrystalline silicon layer from among the inspection beams is greater than 385 nm and equal to or less than 410 nm.

11. The device as claimed in claim 8, wherein
the polycrystalline silicon layer is measured by at least one of reflectivity measurement, Raman spectroscopy, and spectroscopic ellipsometry.

12. A method for inspecting a polycrystalline silicon layer that is crystallized by receiving irradiated laser beams on a front side of the polycrystalline silicon layer, the method comprising:
   emitting inspection beams to a rear side of the polycrystalline silicon layer, wherein the front side of the polycrystalline silicon layer includes a plurality of crystallized protrusions; and
   inspecting and analyzing the inspection beams reflected on the polycrystalline silicon layer.

13. The method as claimed in claim 12, wherein
the rear side of the polycrystalline silicon layer contacts a buffer layer or a substrate and is parallel with the buffer layer or substrate.

14. The method as claimed in claim 13, wherein
the polycrystalline silicon layer is crystallized starting from the front side, and
an area near the rear side of the polycrystalline silicon layer is in an amorphous or microcrystalline state.

15. The method as claimed in claim 13, wherein
the laser beams crystallizing the polycrystalline silicon layer are excimer laser beams.

16. The method as claimed in claim 13, wherein
the buffer layer or the substrate is made of a material including silicon.

17. The method as claimed in claim 13, wherein
the buffer layer or the substrate, together with the polycrystalline silicon layer, has transmittance that is greater than 5%.

18. The method as claimed in claim 12, wherein
the polycrystalline silicon layer has a thickness within the range of 10 nm to 300 nm.

19. The method as claimed in claim 12, wherein
the inspection beams include at least one of ultraviolet (UV) rays, infrared rays, and laser beams.

20. The method as claimed in claim 19, wherein
a wavelength with a reflective index that is less than 50% from among the inspection beams in the polycrystalline silicon layer is used for measurement.

21. The method as claimed in claim 19, wherein
a wavelength used to measure the polycrystalline silicon layer from among the inspection beams is greater than 385 nm and equal to or less than 410 nm.

22. The method as claimed in claim 19, wherein
the polycrystalline silicon layer is measured by using at least one of reflectivity measurement, Raman spectroscopy, and spectroscopic ellipsometry.

* * * * *